(12) United States Patent  
Han

(10) Patent No.: US 9,219,223 B2  
(45) Date of Patent: Dec. 22, 2015

(54) PIEZOELECTRIC CRYSTAL ELEMENTS OF SHEAR MODE

(75) Inventor: Pengdi Han, Naperville, IL (US)

(73) Assignee: CTG ADVANCED MATERIALS, LLC, Bolingbrook, IL (US)

( * ) Notice: Subject to any disclaimer, the term of this patent is extended or adjusted under 35 U.S.C. 154(b) by 1129 days.

(21) Appl. No.: 13/025,751

(22) Filed: Feb. 11, 2011

(65) Prior Publication Data

US 2011/0215676 A1  Sep. 8, 2011

Related U.S. Application Data

(63) Continuation of application No. 12/252,037, filed on Oct. 15, 2008, now Pat. No. 7,908,722, which is a continuation of application No. 11/818,735, filed on Jun. 15, 2007, now abandoned, which is a continuation of application No. 11/182,704, filed on Jul. 14, 2005, now abandoned.

(60) Provisional application No. 60/598,885, filed on Jul. 14, 2004.

(51) Int. Cl.
| | |
|---|---|
| H01L 41/09 | (2006.01) |
| H01L 41/16 | (2006.01) |
| H01L 41/187 | (2006.01) |
| H01L 41/29 | (2013.01) |
| H01L 41/257 | (2013.01) |
| H01L 41/338 | (2013.01) |
| G01C 19/5607 | (2012.01) |

(52) U.S. Cl.
CPC ........ *H01L 41/1875* (2013.01); *H01L 41/0986* (2013.01); *H01L 41/0993* (2013.01); *H01L 41/1876* (2013.01); *H01L 41/257* (2013.01); *H01L 41/29* (2013.01); *H01L 41/338* (2013.01); *G01C 19/5607* (2013.01); *H01L 41/0906* (2013.01); *Y10T 29/42* (2015.01); *Y10T 29/49005* (2015.01); *Y10T 29/49155* (2015.01)

(58) Field of Classification Search
CPC ............ H01L 41/1875; H01L 41/1876; H01L 41/257; H01L 41/29; H01L 41/338; H01L 41/0906; H01L 41/0986; H01L 41/0993; G01C 19/5607; Y10T 29/42; Y10T 29/49005; Y10T 29/49155
USPC .................. 29/25.35, 594, 846; 252/62.9 PZ; 310/333, 358, 360, 365
See application file for complete search history.

(56) References Cited

U.S. PATENT DOCUMENTS

| | | | |
|---|---|---|---|
| 6,170,330 B1 * | 1/2001 | Nakajima | 73/504.16 |
| 2006/0012270 A1 * | 1/2006 | Han | 310/358 |

FOREIGN PATENT DOCUMENTS

JP           61238113 A  * 10/1986 .................. 29/25.35

* cited by examiner

*Primary Examiner* — A. Dexter Tugbang  
(74) *Attorney, Agent, or Firm* — Andrew F. Young, Esq.; Lackenbach Siegel, LLP

(57) ABSTRACT

Preparations of piezoelectric single crystal elements involving the steps of mechanically finishing a single crystal element with select cuttings, coating electrodes on a pair of Z surfaces, poling the single crystal along the <011> axis under a 500V/mm electric field and a product made by the process thereof.

2 Claims, 11 Drawing Sheets

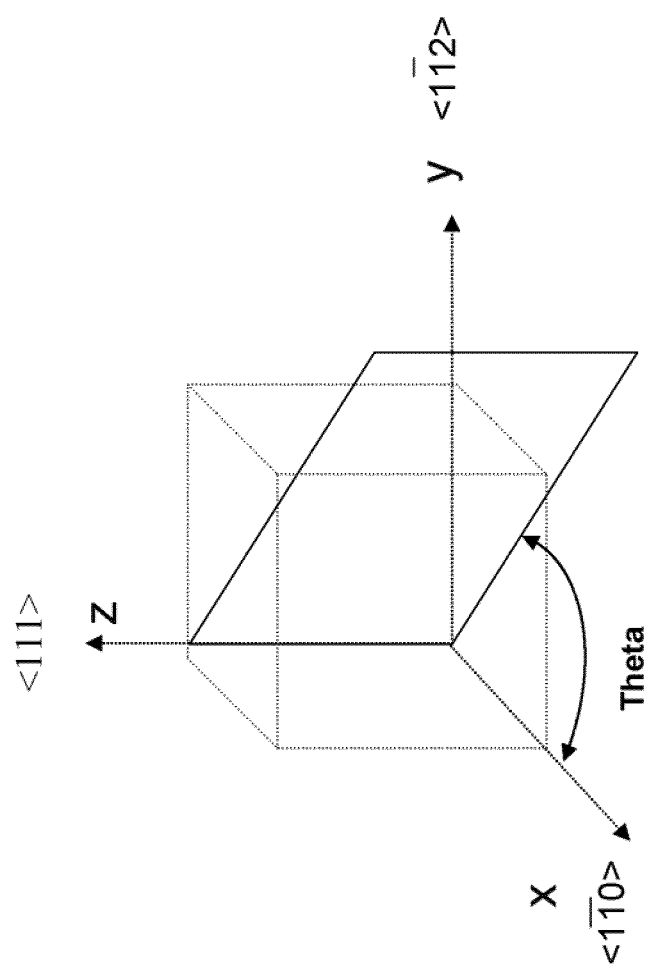

PIEZOELECTRIC CRYSTAL ELEMENTS OF SHEAR MODE

RELATED APPLICATIONS

This application claims priority from U.S. Ser. No. 12/252,037 filed Oct. 15, 2008 issued as U.S. Pat. No. 7,908,722 on Mar. 22, 2011 which is a continuation of and in turn claims priority from U.S. patent application Ser. No. 11/818,735 filed Jun. 15, 2007; which is a continuation of and in turn claims priority from U.S. patent application Ser. No. 11/182,704, filed Jul. 14, 2005; and which in turn claims priority from U.S. Prov. App. Ser. No. 60/598,885 filed Jul. 14, 2004, the contents of each of which are full incorporated herein by reference.

BACKGROUND OF THE INVENTION

1. Field of the Invention

This invention relates to the piezoelectric crystal elements of shear mode and the process for the preparation thereof. The single crystals can be PMN-PT (Lead Magnesium Niobate-Lead Titanate), PZMN-PT (doped PMN-PT), or related piezoceramic materials. More particularly, the present invention relates to the discoveries of the new cut directions that optimize the shear mode piezoelectric properties. In the discovered cut directions, the PMN-PT crystal elements and related compositions have super-high piezoelectric performance with $d_{15}$, $d_{24}$ and $d_{36}$ share mode at room temperature. Even more particularly, the present invention relates to a $d_{15}$ shear mode crystal that gives the maximum d value and is free from the cross-talk of $d_{11}$ and $d_{16}$. A further aspect of the present invention is that the $d_{36}$ mode provides substantial reliability over other shear elements due to its re-poling capability. The crystal elements above can be commercially used for high-sensitive acoustic transducers and in many other applications known to those of skill in the piezoelectric ceramic and ceramic composition arts.

2. Description of the Related Art

The piezoelectric materials are the operational center of acoustic transducers which are broadly used in medical and commercial imaging systems and SONAR systems. The most common types of transducers utilize lead zirconate titanate (PZT) based ceramics as a piezoelectric function. Piezoelectric ceramics convert mechanical energy into electrical energy and conversely electrical energy into mechanical energy. While conventional PZT materials remain the most common materials used in acoustic transduction devices, changing material requirements have fostered the need for new piezoelectric materials having improved dielectric, piezoelectric and mechanical properties.

In THE early 1980s, Kuwata et al. (see J. Kumata, K. Uchino and S. Nomura, *Dielectric and piezoelectric properties of $0.91Pb(Zn_{1/3}Nb_{2/3})O_3$-$0.09PbTiO_3$*, Jpn. J. Appl. Phys., 21, 1298-1302 (1982)) found relatively "high" piezoelectric coefficient, $d_{33}$, of 1500 pC/N and electromechanical coupling factor, $k_{33}$, of 0.92 in 0.91PZN-0.09PT single crystals along <001> direction. The entire disclosure of Kuwata is incorporated herein by reference.

Later, relatively "high" piezoelectric properties were also observed in PMN-PT crystals by Shrout and his co-workers in 1990 (see T. R. Shrout, Z. P. Chang, N. Kim and S. Markgraf, *Dielectric behavior of single crystals near the $(1-x)Pb(Mg_{1/3}Nb_{2/3})O_3$-$xPbTiO_3$ Morphotropic Phase Boundary*, Ferroelectrics Lett., 12, 63-69 (1990)), but substantial limitations remained during application and testing The entire disclosure of Sprout et al., is herein incorporated hereby reference.

Reasonably "high" electromechanical coupling ($k_{33}$)>90%, piezoelectric coefficient ($d_{33}$)>2500 pC/N and increased strain up to 1.7% in <001> orientation (poling along <001> axis) were reproducibly observed in the later 1990's (see S. E. Park and T. R. Shrout, *Ultrahigh strain and piezoelectric behavior in relaxor based ferroelectric single crystals*, J. Appl. Phys., 82, 1804-1811 (1997)). The improved "high" piezoelectric properties noted in this literature promised a new application of acoustic transduction devices using the longitudinal extension mode ($d_{33}$ or compression mode) but failed to achieve the present results. The entire disclosure of S. D. Park is herein incorporated by reference.

The shear mode of piezoelectric vibration is broadly used in acoustic actuators and sensors. For examples, accelerometers utilizing the shear principle have some special advantages compared to the standard compression type accelerometers as they are considerably less strain sensitive to mounting conditions. Unfortunately, the shear piezoelectric coefficient $d_{15}$ for <001> oriented PMN-PT crystals is very small, less than 200 pC/N (see Rui Zhang et al., *Elastic, piezoelectric and dielectric properties of multi-domain $0.67Pb(Mg1/3Nb2/3)O3$-$0.33PbTiO3$ single crystals*, J. Appl. Phys. Vol. 90 (2001) 3471-3475). The entire disclosure of Zhang is herein incorporated by reference.

However, the super-high shear piezoelectric coefficient $d_{15}$ for <111> oriented PMN-PT crystals was discovered as high as 8000 pC/N for PMN-33% PT crystal (Pengdi Han, *Progress in PMN-PT crystal growth*, 2002 U.S. Navy workshop on acoustic transduction materials and devices, 13~15 May, 2002 Penn State.) The entire disclosure of Han is herein incorporated fully by reference. While this piezoelectric coefficient $d_{15}$ is one order higher than that of traditional PZT piezoelectric ceramics (the maximum $d_{15}$ of PZT-5H is typically 750 pC/N), this improvement limited in understanding and nature, as will be discussed hereinbelow.

Soon after, it was confirmed that the $d_{15}$ could be as high as 4100 pC/N for PMN-30% PT crystals (see Rui Zhang et al., *Single domain properties of $0.67Pb(Mg1/3Nb2/3)O3$-$0.33PbTiO3$ single crystals under electric field bias*, Appl. Phys. Letters Vol. 82 No. 5, February (2003)). The entire contents of Zhang et al., are herein incorporated fully by reference. As with Han above, Zhang fails to provide a full understanding of the increased $d_{15}$ measure.

Recently, the $d_{15}$ was also observed as high as 5980 pC/N for PMN-31% PT crystals (see Jue Peng et al., *Shear mode piezoelectric properties of $0.69Pb(Mg1/3Nb2/3)O3$-$0.31PbTiO3$ single crystals*, Solid State Communications 130 (2004) 53-57). The entire contents of Peng et al. are herein incorporated by reference. Peng et al. fails to provide the necessary understanding and additional elements to prevent cross talk and improve reliability.

US 2005/0034519 A1, Feb. 17, 2005 to Ken Kan Deng et al., the entire contents of which are herein incorporated by reference) discloses an acoustic vector sensor, specially an underwater acoustic vector sensor using a shear mode ($d_{15}$) PMN-PT crystal. However, as with each of the disclosures noted above, there is no information of crystal orientation and cut direction details.

In view of the related references, it is clear to those of skill in the art that none provides a report of preparation and application for a d36 shear mode of piezoelectric crystals.

As is also clear from the references themselves, all of the $d_{15}$'s tested or calculated above are based on the common orientation: <111> as poling direction (3 axis) and <110> as applied field direction (1 axis). These references also illustrate the severe lack of investigation to determine an optimum direction (orientations) which give the optimized piezoelectric performance for each piezoelectric vibration modes.

As a consequence, there is a need to both optimize multiple piezoelectric performance indicia and calculate an optimum direction. In response to these needs, in this invention, we report the discovery results of the new cut directions that maximize piezoelectric coefficients, including a d36 mode, for all of the possible symmetric domain configurations of PMN-PT related crystals.

OBJECTS AND SUMMARY OF THE INVENTION

In response to the needs noted herein, it is therefore an object of the invention to provide two kinds of shear mode piezoelectric crystal elements having the maximum of shear piezoelectric coefficient, i.e., coordination rotated d15 and d36 shear mode, and preparation methods therefore. They are:

A xzt-22.5° (±5° cut (<111> poling 3 m) d15 shear mode crystal element free from the cross-talk from d16 and d11.

A zxt±45° (±5° cut (<011> poling mm2) d36 shear mode crystal element having the re-polable characteristics:
    A free X-Y cut (<111> poling 3 m) d15 shear mode crystal element
    A Y-cut d15 shear mode crystal element free from the cross-talk from d16

According to the present invention, the piezoelectric crystal has the general composition represented by the formula:

$$Pb Z_y(Mg_{1/3}Nb_{2/3})_{1-x-y}Ti_xO_3 \quad (1)$$

where y is defined as 0 to 0.10, and x is defined as 0.20 to 0.35, and Z is represented by the one or more dopant elements. The dopant element(s) can be single elements or combinations of one or more of the elements listed in Table 1.

TABLE 1

| Dopants (used alone or in combination) | | | | | | | | | | | |
|---|---|---|---|---|---|---|---|---|---|---|---|
| Zr | Hf | Sn | In | Sc | Tm | Nb | Ta | Zn | Yb | Lu | Sb |
| Bi | Mn | Ga | Ce | Ni | W | Cu | Fe | K | Na | Li | Ba |

The present invention relates to Piezoelectric crystal elements having preferred cut directions that optimize the shear mode piezoelectric properties. In the discovered cut directions, the crystal elements have super-high piezoelectric performance with $d_{15}$, $d_{24}$ and $d_{36}$ shear modes at room temperature. The $d_{15}$ shear mode crystal gives a maximum d value and is free from the cross-talk of $d_{11}$ and $d_{16}$. The $d_{36}$ mode is extremely reliable compared to other shear elements due to its ready re-poling capability. The crystal elements may be beneficially used for high-sensitive acoustic transducers.

In application, the crystal elements above can be commercially used for ultra-sensitive acoustic transducers and sensors, and in other mariners commercial, military, and research orientated as known to those of skill in the art.

The above, and other features and advantages of the present invention will become apparent from the following description read in conduction with the accompanying drawings, in which like reference numerals designate the same elements.

The maximum $d_{15}$ obtained:
    $d_{15}$=5192 pC/N at φ=0°, θ=−22.5°, and ψ=0°
    $d_{15}$=−5192 pC/N at φ=0°, θ=157.5°, and ψ=0°

Figure 2A:
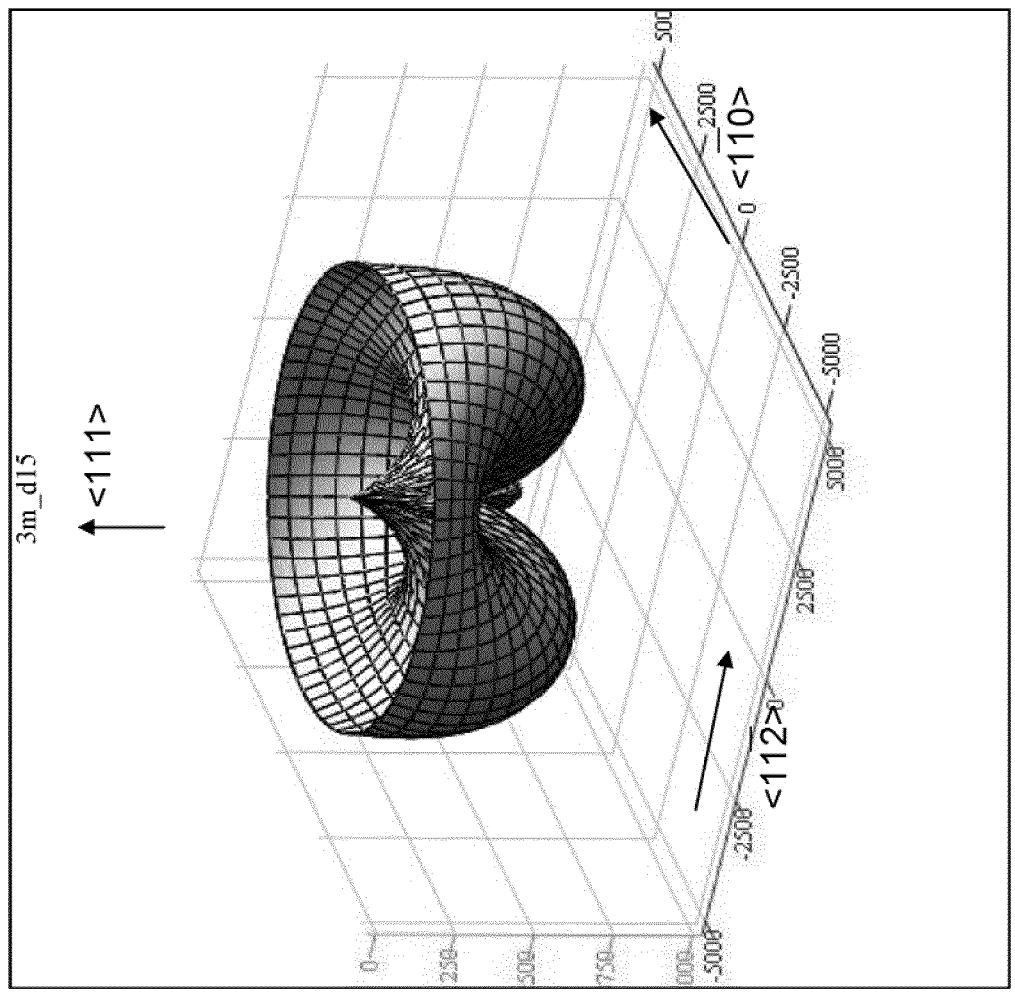

FIG. 2A shows a Z-cut plot of the piezoelectric surface of $d_{15}$.

Figure 2B:
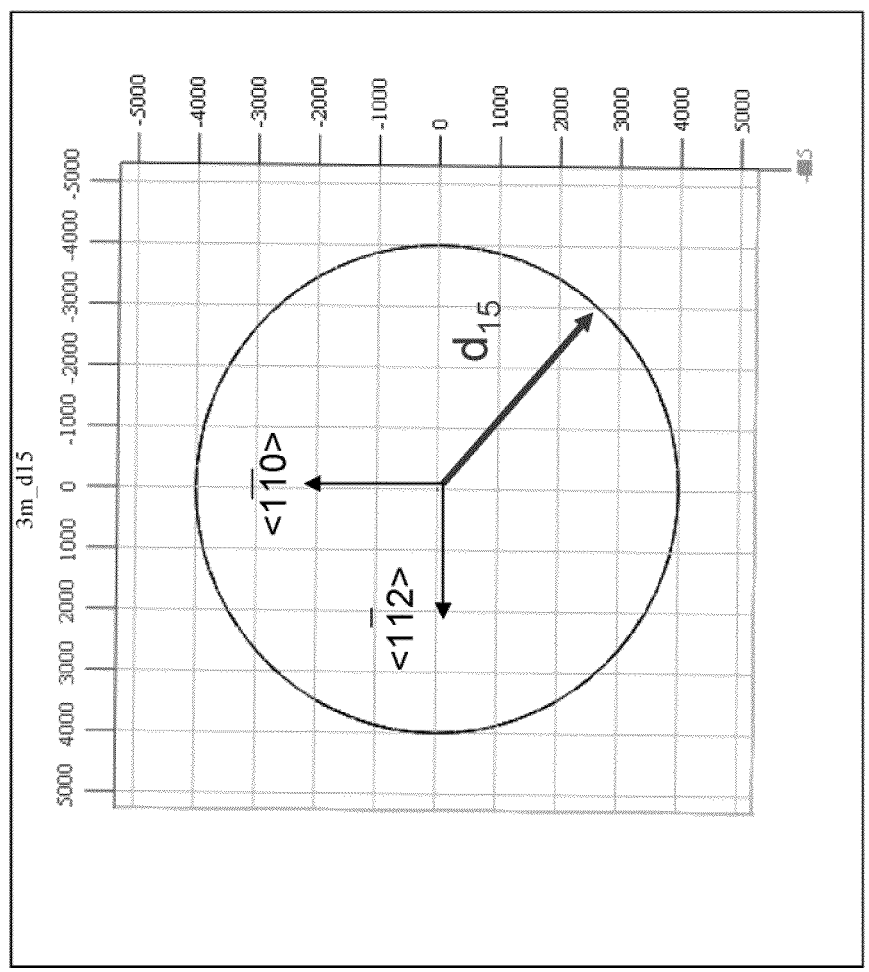

FIG. 2B shows a Z-cut of a 2D plot of the piezoelectric surface of $d_{15}$ indicating the independence of $d_{15}$ from cut direction rotating around Z axis.

FIG. 2C shows the free XY-cut (<111> poling 3 m) for $d_{15}$ mode, angle Theta can be 0~360°.

Figure 3A:
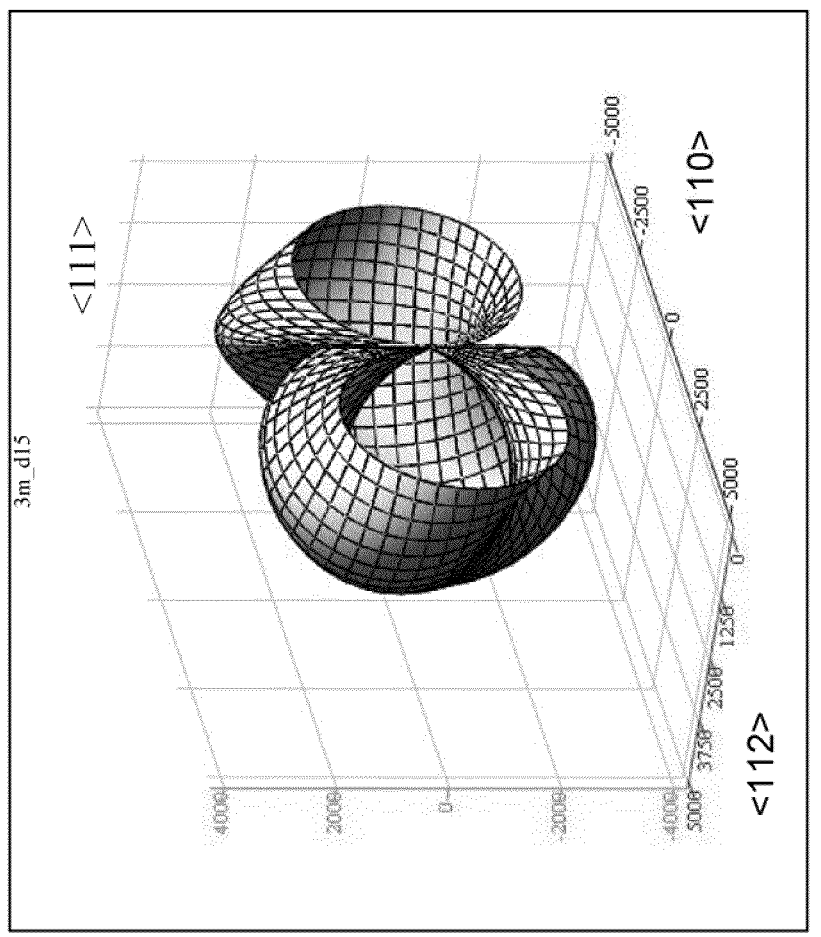

FIG. 3A shows a Y-cut of a 3D plot of the piezoelectric surface of $d_{15}$.

Figure 3B:
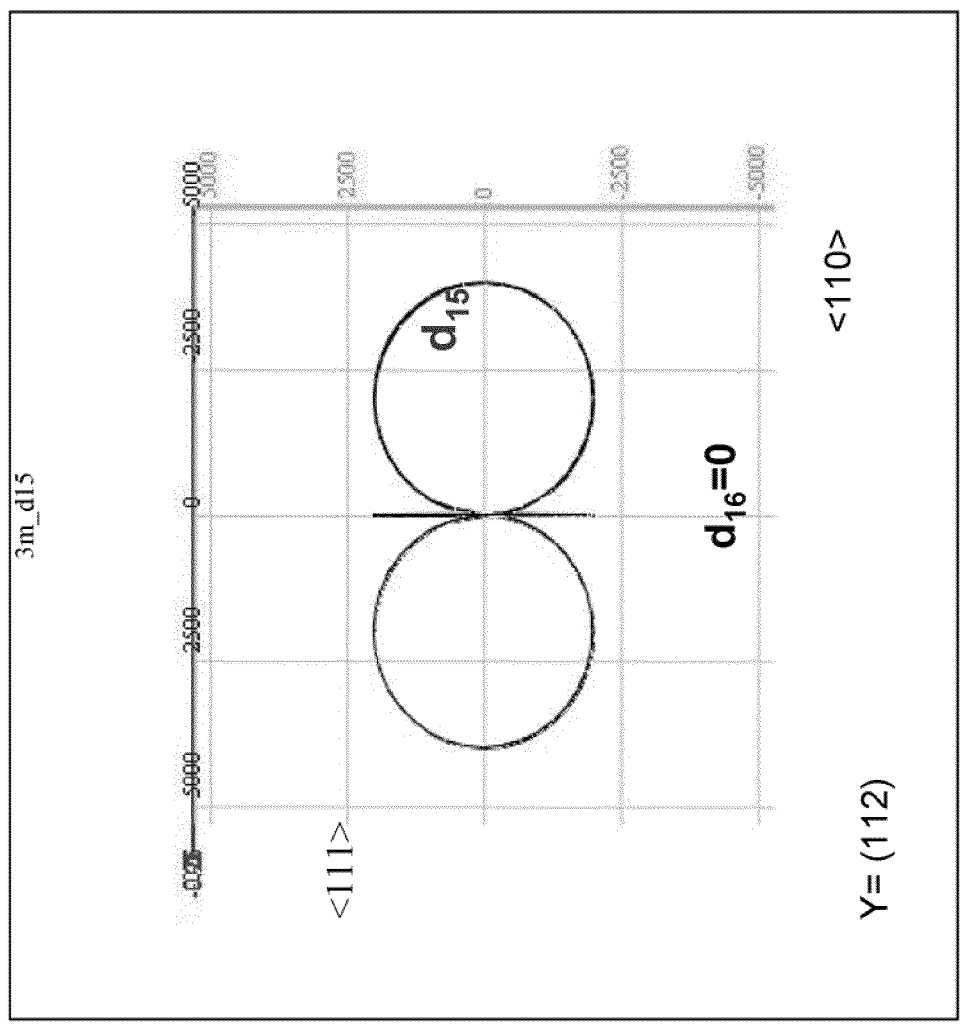

FIG. 3B shows a Y-cut of a 2D plot of the piezoelectric $d_{15}$ which shows a $d_{15}$ free of cross talk from $d_{16}$.

Figure 4A:
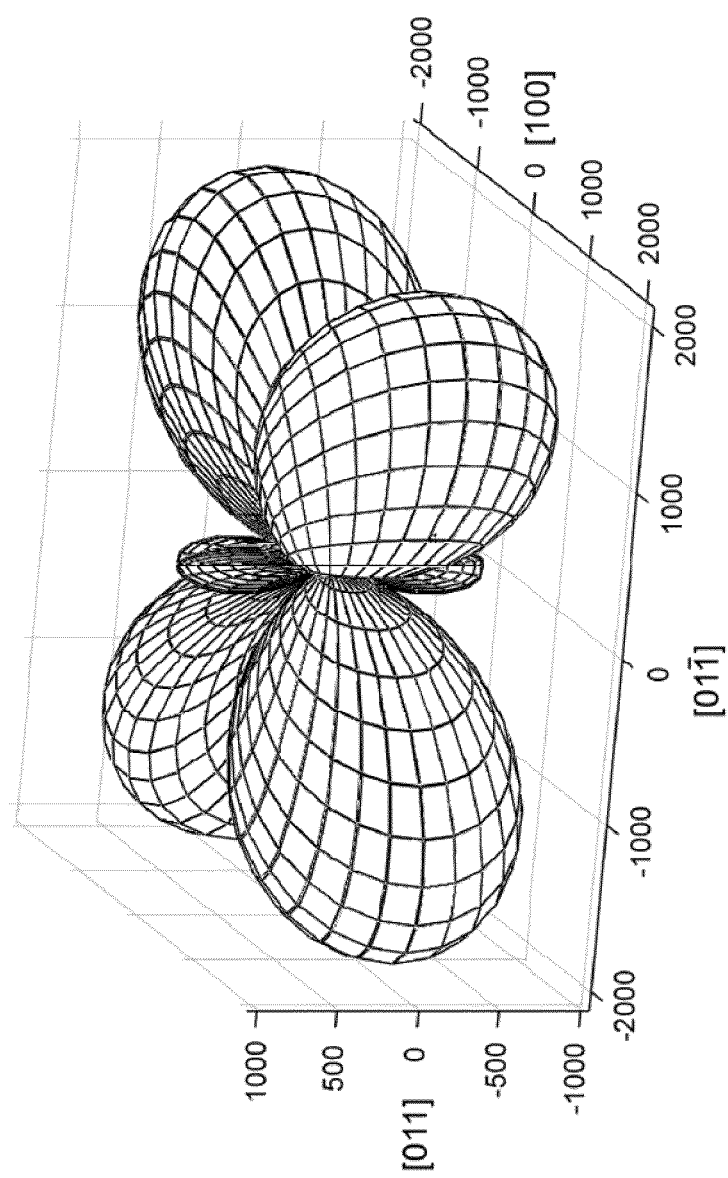

FIG. 4A shows 3D plot of the piezoelectric surface of $d_{36}$. Here, Z=<0,1,1>, X=<1,0,0> and Y=<0,1,−1> and provide a pseudo-cubic notation.

Figure 4B:
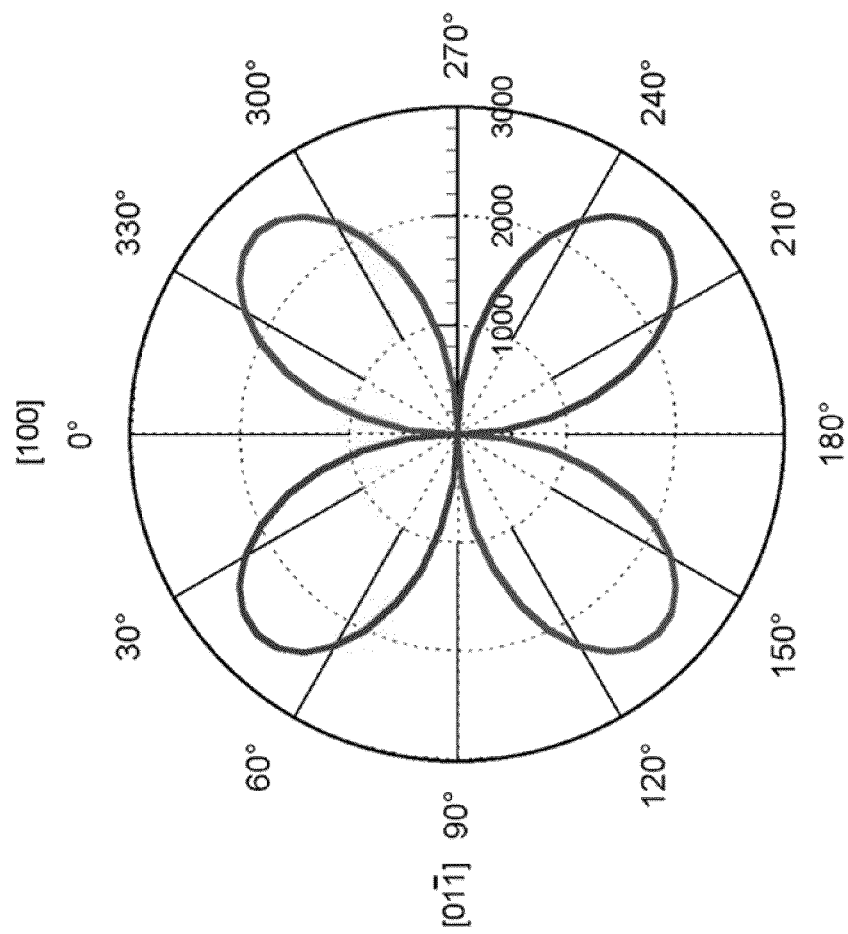

FIG. 4B shows A 2D plot, Z-cut cross section of the piezoelectric $d_{36}$ surface on the (011) plane. The maximum $d_{36}$ obtained:
    $d_{36}$=2600 pC/N at φ=45° or 225°, θ=0°, and ψ=0°.
    $d_{36}$=−2600 pC/N at ψ=135° or 314°, θ=0°, and ψ=0°.

Figure 5:
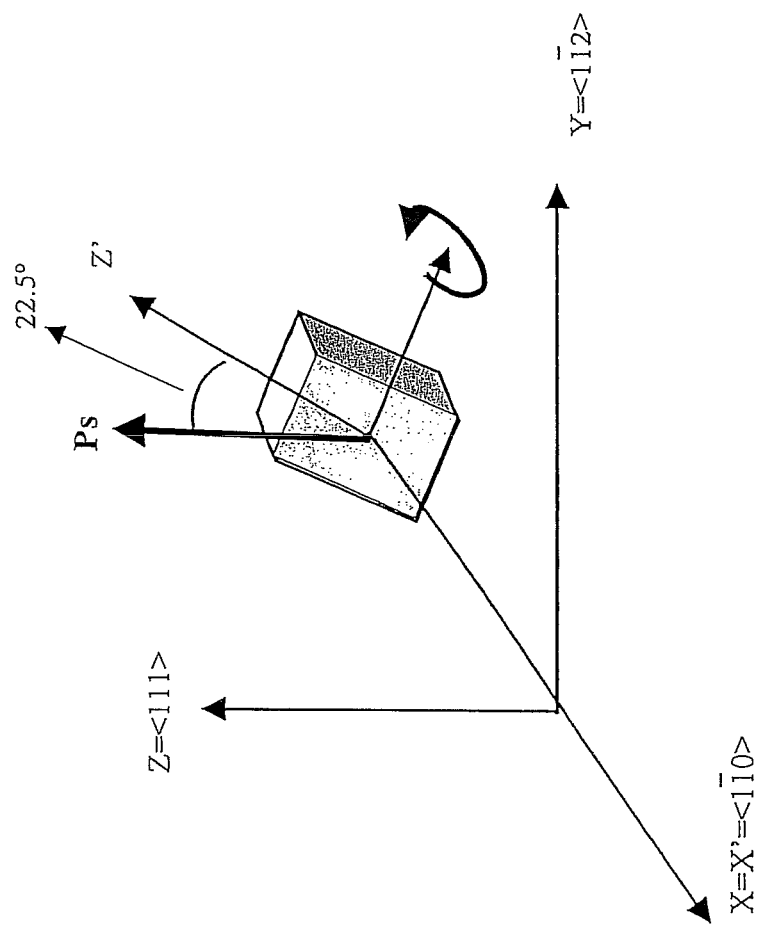

FIG. 5 shows the xzt−22.5° cut of $d_{15}$ mode for <111> poled PMN-PT crystal.

Figure 6:
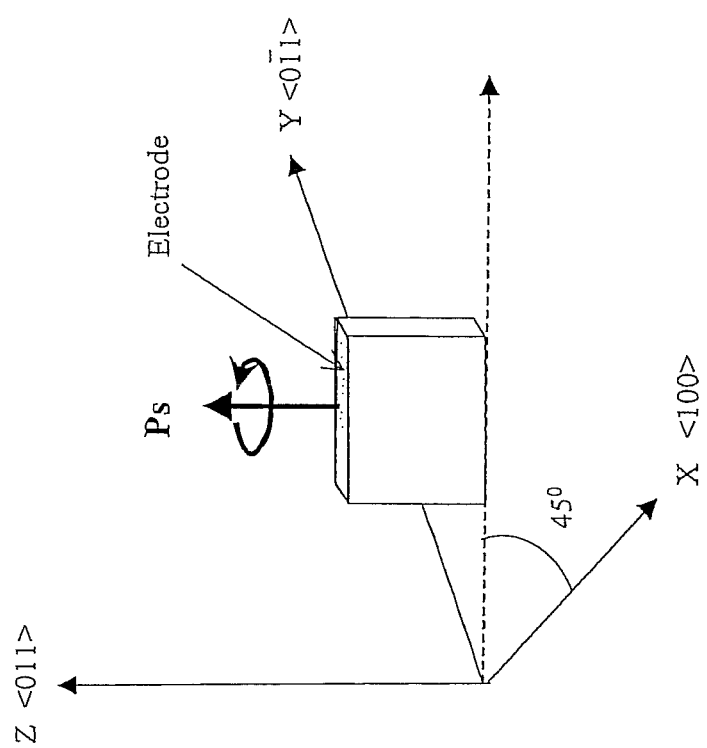

FIG. 6 shows the zxt±45° cut of $d_{36}$ mode for <011> poled PMN-PT crystal.

DETAILED DESCRIPTION OF A PREFERRED EMBODIMENT

The representation surfaces of the piezoelectric strain coefficient (d) were calculated for [011], [001] and [111] poled PMN-PT crystals with ~31% PT. It was discovered that the zxt±45° cut (rotation around z-axis±45° for [011] poled PMN-PT crystal gives a unique "re-poleable" shear piezoelectric coefficient $d_{36}$ up to 2600 pC/N.

The zxt 0° cut (without rotation) $d_{31}$ up to −1750 pC/N was obtained for the [011] poled crystals. It was also found that an extraordinarily high shear piezoelectric coefficient $d_{15}$ up to 5190 pC/N for the single domain crystal (3 m) occurred in the xzt−22.5° cut (22.5° clockwise rotation about x-axis). These calculated results were experimentally verified, as will be discussed.

The transformation of piezoelectric coefficients by changing coordinate system is represented by the following equation:

$$d'_{ijk}=\Sigma a_{il}a_{jm}a_{kn}d_{lmn} \quad (2)$$

where $d_{lmn}$ is the piezoelectric coefficient in the original coordinate system, $d'_{ijk}$ is the piezoelectric coefficient in the new rotated coordinate system, and $a_{il}$, $a_{jm}$ and $a_{kn}$ are the components of the transformation matrix.

The coordinate rotation was defined in the following way: rotation was first made by angle φ around the z-axis, then around the new x-axis by angle θ, and finally around the new z-axis by angle Ψ. All of the rotations were counterclockwise. The new piezoelectric coefficients after the rotation in the 3-dimensional space were derived as functions of the independent piezoelectric coefficients in the original coordinate system and the rotated Euler angles (φ, θ, Ψ) using tensor calculations.

To obtain the independent piezoelectric coefficients, three sets of samples of PMN-31% PT crystal (3 m, mm2, and 4 mm) were prepared to cope with the scattering of the measured data within each set caused by the PT-content variation and the process history.

The coordinates were selected as follows: [1$\bar{1}$1] as z-axis, [110] as x-axis, and [11$\bar{2}$] as y-axis for 3 m symmetry; [011] as z-axis, [100] as x-axis, and [01$\bar{1}$] as y-axis for mm2 symmetry; and [001] as z-axis, [100] as x-axis, and [010] as y-axis for 4 mm, respectively.

An electrical field strength 5 kV/cm for poling was applied along the z-axis at room temperature. As used herein, room temperature ranges roughly from 33° F. to roughly 100° F.

The poling current density was limited within 10 μA/cm² by an automatic DC power supply unit. A complete poling can be achieved by retaining the poling E-field for one minute after setting the poling current back to zero. The independent piezoelectric coefficients of the three engineered multi-domain systems were directly measured using a modified Berlincourt meter with homemade adaptors. After repeated tries employing this setting, it was determined that the present embodiment provides a measurement error within about +5%.

Figure 1A:
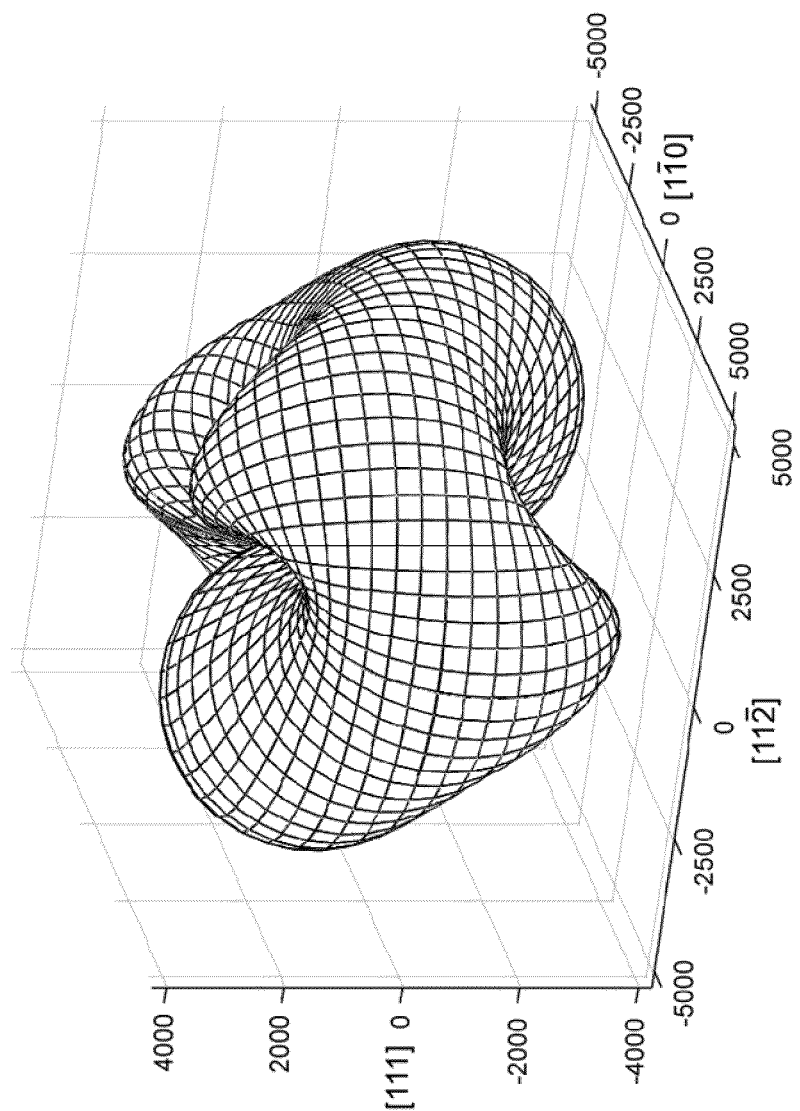
FIG. 1A provides for a transverse shear piezoelectric coefficient, $d_{15}$, a 3D plot of the piezoelectric surface of $d_{15}$. Here, Z=<1,1,1>, X=<1,−1,0> and Y=<1, 1, −2> and provides pseudo-cubic notation.
Figure 1B:
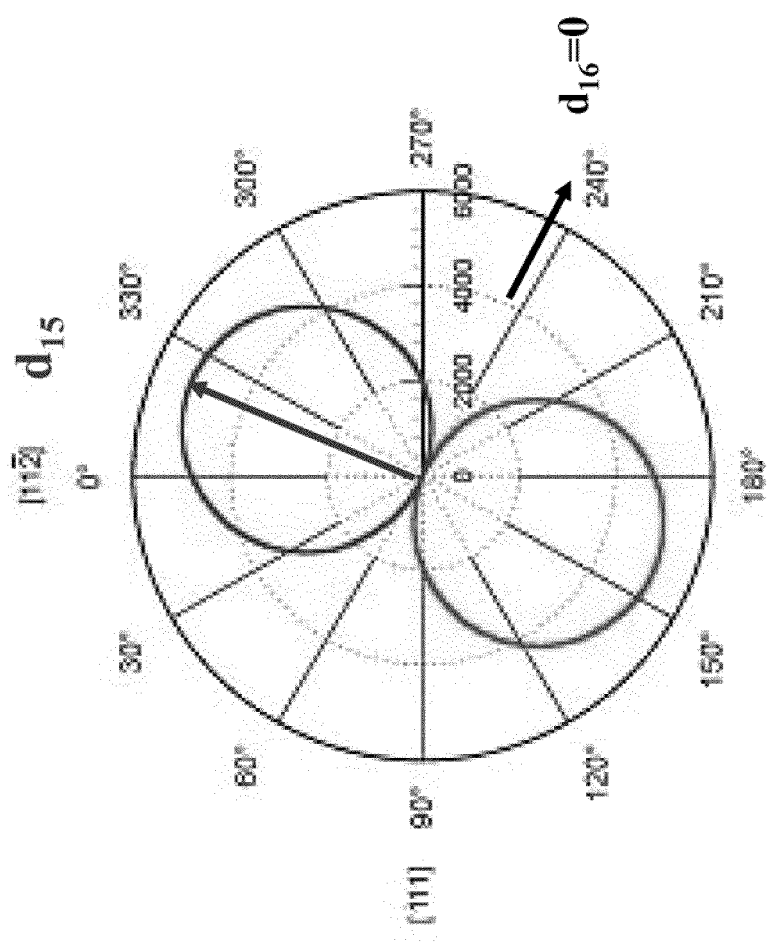
FIG. 1B shows a 2D plot and X-cut cross section of the piezoelectric $d_{15}$ surface on the (110) plane indicating the occurrence of maximum $d_{15}$ and free from $d_{16}$ cross talk.

A single domain PMN-PT crystal (3 m) can be obtained by completely poling along the [111] direction. The single domain crystal has four independent piezoelectric coefficients: $d_{15}$ $d_{24}$), $d_{16}$ (=$2d_{21}$=-$2d_{22}$), $d_{31}$($d_{32}$) and $d_{33}$. The representation surface of the shear piezoelectric coefficient $d_{15}$ was then calculated, and is represented in FIG. 1. As shown, the amplitude of the surfaces represents the absolute value of the piezoelectric coefficient in that orientation.

The maximum value of $d_{15}$ of 5190 pC/N is in the direction of θ of 337.5° and φ of 0° (xzt-22.5°). The maximum amplitude of $d_{15}$ (-5190 pC/N) was found at θ of 157.5° and φ of 0° (xzt 157.5°). The maximum $d_{15}$ value in the rotated coordinate is approximately 1.1 times the original $d_{15}$. Particularly, the cross talk from $d_{16}$ is eliminated for the rotated coordinate. In contrast, strong cross talk between $d_{15}$ (4800 pC/N) and $d_{16}$ (1975 pC/N) exists before the rotation.

The shear piezoelectric coefficient $d_{36}$ is a dependent tensor and is zero in original coordinate circumstances. To explore the maximum value of $d_{36}$ in a rotated coordinate system, the representation surface of the shear piezoelectric coefficient $d_{36}$ was calculated and this is shown as FIG. 4.

The maximum $d_{36}$ (±2600 pC/N) was obtained in the direction of θ of 0° and φ of ±45° (zxt±45°) or ±225°.

In an effort to verify the above maximum values from theoretical calculation, four groups of samples were prepared by cutting in the rotation angle where the maximum d values had occurred. The measured maximum d values confirmed the calculation results, which are summarized in Table 1 in context with the four types of vibration modes. The calculation on 4 mm multi-domains was not presented in this work, as it has been initially described in a limited manner. described in references hereinabove and is incorporated here fully by reference.

It can be seen from the good consistency between the calculated results and the measured data in Table 1, that the present invention is easily verified as valid.

TABLE 1

Provides a comparison between experimental value and calculated data that validates the present invention.

| Vibration Mode | Longitudinal Extension | Transverse Extension | Longitudinal Shear | Transverse Shear |
|---|---|---|---|---|
| poling |  |  |  |  |
| Stress |  |  |  |  |
| Symmetry | 4 mm | mm 2 | mm 2 | 3 m |
| Cut direction | zxt 0° | zxt 0° | zxt ±45° | xzt -22.5° |
| Calculated value (pC/N), 31% PT | $d_{33}$ 2000 | $d_{31}$ -1750 | $d_{36}$ 2600 | $d_{15}/d_{16}$ 5190/0 |
| Measured value (pC/N), 31% PT | $d_{33}$ 2000 | $d_{31}$ -1750 | $d_{36}$ 2520 | $d_{15}/d_{16}$ 5300/60 |

Referring now to FIG. 5, a process for preparation of the single crystal element of the present invention comprises at least the steps:
  (a) poling a single crystal with a selected composition, in the direction along the <111> cubic axis under 500V/mm electrical field at room temperature;
  (b) mechanically finishing of the single crystal elements with cuttings such as xzt-22.5°, ±5°; and
  (c) coating working electrodes on both X surfaces and removing the poling electrodes on both Z surfaces.

Referring now to FIG. 6, an alternative is provided for preparation of the single crystal elements described herein which comprises the steps:
  (a) mechanically finishing of the single crystal elements with cuttings such as zxt±45° (±5°);
  (b) coating electrodes on a pair of Z surfaces; and
  (c) poling the single crystal in the direction along the <011> cubic axis under 500V/ram electrical field at room temperature.

A variety of experiments were conducted to test the above considerations. These experiments are discussed below.

Experiment 1

A plate crystal element, similar to that shown in FIG. 5, was created and measured data of $d_{15}$ as high as 6,000 pC/N, and $d_{16}$ less than 100 pC/N, and $d_{11}$ less than 90 pC/N.

Experiment 2

A plate crystal element, constructed as shown in FIG. 6, was measured and provided measured data of $d_{36}$ as high as 2,000 pC/N and $d_{34}d_{35}$ less than 50 pC/N. The $d_{36}$ shear mode crystal elements was easily be re-poled, if any de-poling occurred or was necessary.

Experiment 3

The plate crystal element as FIG. 2, was provided wherein the rotation angle theta was taken from 0 to 330° in increments of 30°. The measured data of $d_{15}$ are listed in Table 2.

TABLE 2

Experiment data for free X-Y cut (<111> poling 3 m) $d_{15}$ shear mode crystals

| Theta° | 0° | 30° | 60° | 90° | 120° | 150° |
|---|---|---|---|---|---|---|
| $d_{15}$ pC/N | 3940 | 3720 | 4050 | 3870 | 4100 | 4220 |

TABLE 2-continued

Experiment data for free X-Y cut (<111> poling 3 m)
$d_{15}$ shear mode crystals

| Theta° | 180° | 210° | 240° | 270° | 300° | 330° |
|---|---|---|---|---|---|---|
| $d_{15}$ pC/N | 4190 | 3788 | 4240 | 3870 | 4301 | 3904 |

Experiment 4

In this experiment, a plate crystal element, as shown in FIGS. 3A and 3B provided measured data of $d_{15}$ as high as 4400 pC/N and $d_{16}$ less than 100 pC/N.

Those of skill in the art should understand, that crystal cutting orientation are described with PRE notation. Those of skill in the crystal forming arts should additionally understand that the $d_{ij}$ parameters were measured on a Berlincout type meter with an adapter and dielectric constant measured on a HP-4294A Impedance Analyzer.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

What is claimed is:

1. A piezoelectric single crystal product made by the process of:
    (a) providing a piezoelectric crystal element with a cutting direction along zxt±45°;
        (i) said single crystal element providing a $PbZ_y(Mg_{1/3}Nb_{2/3})_{1-x-y}Ti_xO_3$; wherein Y is defined as from 0 to at least 0.10, X is defined as 0.20 to at least 0.35, and Z is defined as at least one doped element selected from the group consisting of Zr, Hf, Sn, In, Sc, Tm, Nb, Ta, Zn, Yb, Lu, Sb, Bi, Mn, Ga, Ce, Ni, W, Cu, Fe, K, Na, Li, and Ba;
    (b) said single crystal element made by mechanically finishing said single crystal with cuttings along zxt±45°;
    (c) coating electrodes on a pair of Z surfaces;
    (d) poling said single crystal element to a first poled state in the direction along <011> cubic axis under at least a 500V/mm electrical field at room temperature and forming a poled single crystal element; and
    (e) providing said poled single crystal element with an operable $d_{36}$ shear mode and having a $d_{36}$ value up to about 2000 pC/N at room temperature.

2. A piezoelectric single crystal product made by the process, according to claim 1, further comprising the step of:
    (f) repoling said poled single crystal element in said first poled state to a second polled state.

* * * * *